United States Patent [19]
Bringloe

[11] Patent Number: 4,765,478
[45] Date of Patent: Aug. 23, 1988

[54] DISPENSER FOR VISCOUS MEDICANT

[75] Inventor: Keith D. Bringloe, Ware, United Kingdom

[73] Assignee: Smith and Nephew Associated Companies plc, United Kingdom

[21] Appl. No.: 93,993

[22] Filed: Sep. 8, 1987

[30] Foreign Application Priority Data

Sep. 20, 1986 [GB] United Kingdom ............... 8622698

[51] Int. Cl.$^4$ ........................................... A61M 35/00
[52] U.S. Cl. .................................. 206/440; 604/289; 604/290; 604/304; 604/309
[58] Field of Search ............... 604/289, 290, 304, 309; 128/156; 206/440, 441

[56] References Cited

U.S. PATENT DOCUMENTS

| 1,671,825 | 5/1928 | Johnson | 206/440 |
| 4,695,277 | 9/1987 | Lauk | 128/156 |
| 4,710,191 | 12/1987 | Kwiatek et al. | 604/304 |

Primary Examiner—Carroll B. Dority, Jr.
Attorney, Agent, or Firm—Jacobs & Jacobs

[57] ABSTRACT

A dispenser for a viscous pharmaceutical composition comprises a tray, a support layer, a viscous pharmaceutically acceptable carrier which optionally contains a medicament and a removable protector layer. The support layer covers the base and at least two opposed sides of the tray and is capable of extending over the top edges of the said sides of the tray so that stiffening means may be fitted to the extended portion. A viscous pharmaceutically acceptable carrier overlies the support layer and may be lifted from the tray on the support layer using the stiffening means as handles. A removable protector layer covers the exposed surface of the carrier on the tray. The carrier adheres more strongly to the support layer than to the protector layer so that the latter may be peeled from the carrier without disturbing it on the support layer. Preferably the carrier contains from 1 to 12.5% by weight of antibacterial agent.

17 Claims, 1 Drawing Sheet

DISPENSER FOR VISCOUS MEDICANT

The present invention relates to a dispenser for a medicament contained in a viscous pharmaceutically acceptable carrier and more particularly to a dispenser which comprises a tray containing a support layer upon which lies the pharmaceutically acceptable carrier.

The treatment of skin lesions such as burns and wounds to prevent bacterial contamination commonly involves the topical application of an antimicrobial-containing cream or ointment. One such cream which has proved particularly effective is Flamazine (Trade Mark) available from Smith and Nephew Pharmaceuticals Ltd, and which contains silver sulphadiazine as the active antimicrobial agent. Creams are usually spread by hand over the affected area and then covered by strips of gauze. This procedure may be painful, time consuming and provides only a variable and indeterminate dose. Another method of applying such creams is to impregnate a gauze with the antimicrobial composition and apply that to the affected area, see for example U.S. Pat. No. 4,018,186. Such dressings can also be painful and time consuming to apply and also run the risk of being accidentally contaminated during preparation or just prior to use. It has also been noted that in water based systems, the material of the gauze may act as an absorbent for water thereby affecting the integrity of the cream and the release characteristics of any medicament contained in the cream.

A further method of applying a viscous pharmaceutical composition such as a cream may be by means of a spray dispenser, see for example U.S. Pat. No. 4,551,139. This method avoids the disadvantage of being time consuming to apply. An aerosol method of application may be painful because of the high pressure of delivery, the nature of the propellant and the occurrence of intermittent flow of cream due to the introduction of air into the pump flow course. There is also a risk of introducing contaminants into the flow system which may cause problems of wound sepsis. A spray system may also be wasteful in terms of not evacuating all the cream from the container.

It would be an advantage therefore to provide a means of dispensing viscous compositions such as antimicrobial creams in a manner which was substantially painless, quick, simple and with reduced risk of contamination. Such a means of dispensing has now been achieved in which a viscous pharmaceutically acceptable carrier is present on a support layer both held in a tray The carrier prior use is covered by a removable protector layer. The support layer preferably extends over two opposed edges of the tray so that handles may be fitted to the support layer whereby after removal of the protector the support layer and the viscous composition may be lifted as one from the tray. This means that the viscous carrier may be applied to the patient with reduced risk of contamination and without applied pressure of any kind. It is also an advantage that a known weight of the medicament may be applied in this way, which is safer for the patient and more economical in the use of the composition.

Accordingly the present invention provides a dispenser for a viscous pharmaceutical composition which dispenser comprises a tray, a support layer which covers the base and at least two opposed sides of the tray and is capable of extending over the top edges of said sides of the tray, a viscous pharmaceutically acceptable carrier which optionally contains a medicament and which overlies the support layer and a removable protector layer covering the exposed surface of the pharmaceutically acceptable carrier and in which the pharmaceutically acceptable carrier adheres more strongly to the support layer than the protector layer.

Aptly the tray may be formed from a vacuum mouldable polymeric material including a high density polyethylene or a polypropylene-polyethylene copolymer. Suitably these polymers will not be wetted by the pharmaceutical carrier thereby enabling the pharmaceutical carrier to be lifted on its support layer from the tray without leaving unacceptably large amounts of the carrier adhering to the sides of the tray and so being wasted.

The tray may be any shape but is preferably rectangular or square. The tray may be any convenient size but sizes of 18 cm×24 cm, 24 cm×36 cm and 18 cm×18 cm and which have a depth of from 2.5 to 8 mm and preferably 3 to 6 mm, for example 4 mm, have been found to be suitable for containing a pharmaceutically acceptable carrier containing a therapeutically effective amount of medicament.

Suitably the support layer may comprise any material which is capable of supporting the weight of the pharmaceutical carrier without tearing or undue distortion and which may be peeled from the carrier so that substantially none of the carrier remains adhered to the support layer. In use it is envisaged that the pharmaceutical carrier will be applied to a patient's skin or to a conventional surgical gauze dressing so it is important that the pharmaceutical carrier adheres to the skin or gauze more strongly that it adheres to the support layer so that the support layer may be peeled from the carrier without unduly disturbing the carrier on the skin or the dressing. Preferably the support layer should be able to peel back on itself so as to minimise loss of carrier. Therefore the support layer should be flexible and may be coated on one side with a release-coat layer such as a silicone layer, for example the support layer could be a siliconised release paper. However, it is preferred if the support layer is formedfrom a polymeric material and in particular it is preferred if the support layer is in the form of a woven, non woven, knitted or net-like fabric. In one preferred form the support layer is polyester non-woven fabric. In a second preferred form the support layer is a net-like material which has been formed by stretching of an embossed film to cause fibrillation as described in for example, U.K. Pat. Nos.: 914489, 1055963, 1075487, 1110051, 1495151, 1496786 and 1531715.

Aptly the size of the support layer is such that it covers the bottom and two sides of the tray and is capable of extending over the edges of the tray on two opposed edges. The extended support layer is aptly provided with a stiffening means at each of the two edges whereby the stiffening means may be used as handles to lift the support layer and the pharmaceutical carrier from the tray. The support given by the handles also prevents wrinkling of support layer. It has been observed that if the support layer wrinkles and air is admitted between the carrier and the support layer, upon inversion the carrier tends to prematurely separate from the support layer. The handles may be held in place by folding the extra support layer around each handle and then sealing into place. Suitably the handles may be made from waterproof, stiff paper or from polymeric material. When packaged the extended support layer may be folded on top of the protector layer for neatness.

The handles may be permanent, that is present as strips heat sealed into the support layer or they may be positioned just prior to lifting the support layer from the tray and be retrieved for further use.

The pharmaceutical carrier will be sufficiently viscous to be self-supporting that is it will not flow when it is removed from the tray on its supporting layer.

Suitable forms of the topical composition of this invention include ointments, gels, creams, viscous emulsions, pastes, and the like which are capable of being self supporting.

Preferably the composition will be in the form of an ointment and most preferably as a hydrophilic ointment such as an oil-in-water emulsion. Suitable bases are described in Chapter 87 Ointments: Emulsion Bases in Remingtons Pharmaceutical Sciences, 15th Ed. 1975, pages 1532–34. Other suitable ointment bases include those described in British Pat. No. 1240545.

A particularly suitable ointment base is therefore an oil-in-water emulsion containing from 0 to 25% of petrolatum or liquid paraffin, 2 to 20% of a fatty alcohol, 0 to 12% of an emulsifying agent, up to 10% of non-ionic surfactant and 5 to 25% of a polyhydric alcohol and the balance at 100% being water, preferably deionised or distilled water. Aptly the fatty alcohols are those conventionally used in ointments and are water insoluble. Suitable alcohols include stearyl alcohol, cetyl alcohol, lauryl alcohol and myristyl alcohol. Suitably the emulsifying agent is a glyceryl fatty acid ester and is peferably glyceryl monostearate. Suitable non-ionic surfactants include the polyoxyethylated sorbitan fatty acid esters and sorbitan fatty acid esters. An emulsifying wax may be used in place of both or part of both of the fatty alcohol and non-ionic surfactant. The polyhydric alcohol acts as a humectant and suitable alcohols include propylene glycol, sorbitol or glycerin or mixtures thereof.

An alternative ointment may contain one or a mixture of polyalkylene glycols for example polyethylene glycol. Suitably the ointment may contain a mixture of a high molecular weight polyethylene glycol and a low molecular weight polyethylene glycol.

The compositions used in the present invention may be in the form of an aqueous gel. Suitable gelling agents include polyoxyethylene-polyoxypropylene diol block copolymers, polyacrylic acid lightly cross-linked with triallyl sucrose which has been neutralised using an alkali metal hydroxide, cellulosic derivatives such as carboxymethyl cellulose, hydroxymethyl cellulose, natural gums and the like. A preferred group of gelling agents are the polyoxyethylene-polyoxypropylene diol block copolymers which are commercially available as the Pluronics from BASF-Wyandotte. (Pluronic is a registered trade mark of BASF-Wyandotte).

Suitable gel forming block copolymers of polyoxyethylene-polyoxypropylene will have a molecular weight from 4,600 to 13,500 (approximately) and will be present in the gel in an amount from 50% for the lower molecular weight copolymers to 20% for the higher molecular weight copolymers, so that the gel when applied topically is neither too stiff nor too fluid. Typically the gels are formed by mixing together the copolymer and water to form an aqueous solution at a temperature of 2° C. and adding the medicament and then allowing the solution to gel as it warms to ambient temperature. Suitable Pluronics are those designated as F108, F127 and P105.

Alternatively the gel may be formed from a natural gum as described in U.K. Pat. Nos. 1,341,999, 1,593,953 and 1,593,954 or a synthetic gel formed from cross-linked polyoxyalkylene polymers as described in U.S. Pat. No. 3,419,006.

The composition used in the present invention may also be in the form of a hydrophobic ointment. Suitable hydrophobic ointments are those which are formed from white or yellow soft paraffin or a mixture of such with liquid paraffin. A preferred ointment base comprises a mixture of white soft paraffin and liquid paraffin in a ratio of 5:1 to 1:1. However, in general terms aqueous based systems will be preferred.

The hydrophobic ointment base may also contain non-ionic surfactants such as polyoxyethylated sorbitan fatty acid esters and sorbitan fatty acid esters. The presence of non-ionic surfactants increases the miscibility of the ointment with wound fluid and aids release of the medicament. Suitably the non-ionic surfactant will be present in an amount from 0.1 to 0.5%. Preferably the non-ionic surfactant is 0.1% of polyoxyethylene sorbitan triolate and 0.1% sorbitan monopalmitate.

Normally the pharmaceutical carrier will contain medicament but it is envisaged that bland compositions such as emollient creams and barrier creams could be applied using the dispenser of the present invention.

The medicament present in the pharmaceutically acceptable carrier may be any one of those which may be topically applied to the skin including, steroids, debriding agents, wound healing promoters, local anaesthetics, antibacterial agents, antibiotics and like. Preferably the medicament will comprise antibacterial agent. Suitable antibacterial agents include iodophors such as polyvinyl pyrrolidone-iodine, chlorhexidine and its salts such as the diacetate, digluconate and dihydrochloride, silver compounds such as silver sulphadiazine and compatible mixtures thereof such as mixtures of silver sulphadiazine and chlorhexidine diacetate.

The carrier will contain a therapeutically effective amount of medicament. Thus for example in a preferred embodiment the carrier will comprise an ointment containing antibacterial agent at a concentration of, for example, 1 to 12.5% by weight based on the weight of the carrier.

The dose of a medicament may be controlled by thickness of the pharmaceutical carrier layer and/or the concentration of the medicament in the carrier.

The exposed surface of the pharmaceutical carrier when in position in the tray is aptly covered by a protector layer. Thus preferred protector layers are silicone-coated release paper or a net-like material.

The pharmaceutically acceptable carrier will adhere more strongly to the support layer than to the protector layer when the latter is peeled or lifted from the surface of the carrier. This means that in use when the protector layer is peeled from the surface of the carrier the carrier remains relatively undisturbed and does not lift from the support layer.

The dispensers of the present invention may be prepared by vacuum forming the tray in the appropriate size, placing the support layer in the tray and filling the pharmaceutically acceptable carrier onto the support layer. The protector layer is then placed on top of the pharmaceutical carrier.

The dispenser of the present invention is preferably sterile and may be packaged in a bacteria-proof and water-proof package. The dispenser and contents may be sterilised by means of gamma-irradiation or alternatively the dispenser and contents may be assembled under aseptic conditions from presterilised components.

In use this dispenser is removed from its package in sterile form. The protector layer is peeled from the pharmaceutical carrier and the pharmaceutical carrier is lifted from the tray on its support layer by means of the two handles at opposed edges of support layer. The pharmaceutical carrier is then applied to the patient or on to a dressing by carefully inverting the pharmaceutical carrier-support layer and placing the pharmaceutical carrier against the appropriate surface. The support layer may be peeled away from the pharmaceutical carrier (or less preferred left in place). The pharmaceutical carrier may then be covered with a conventional gauze bandage.

In an alternative though less preferred manner of use the support layer could be used next to the wound where the support layer would serve as a non-adherent wound contact layer. In this instance the support layer is preferably formed from a polymeric material such as a net.

In another aspect the present invention provides a method of treating an animal by applying to the skin of the animal a pharmaceutically acceptable carrier from a dispenser as hereinbefore defined.

Preferred embodiments of a dispenser of the present invention will now be described with reference to the drawings in which.

Figure 1:
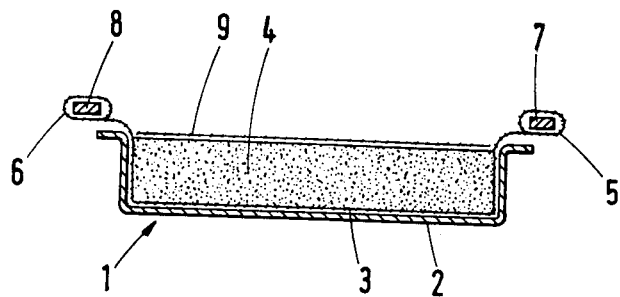
FIG. 1 is a cross-section through a dispenser of the present invention.

The dispenser (1) for a topically applied pharmaceutical composition which is shown in FIG. 1 comprises a tray (2) which is suitably vacuum moulded from high densitypolyethylene or from a polypropylene-polyethylene copolymer. The tray (2) is lined with a support layer (3) which is in the form of a net-like material formed by stretching an embossed film and is available as for example Net 909 P520 from Smith and Nephew Plastics Ltd, Gilberdyke, Hull (Net 909 is a Trade mark). A medicated pharmaceutically acceptable oil-in-water emulsion ointment (4) is filled into the tray (2) to overlay the support layer (3) and to substantially fill the tray (2). The extra pieces of support layer (5,6) are fitted with stiffening means (7,8) in the form of narrow waterproof cardboard strips which are sealed into the extra pieces (5,6) of the support layer (3). These handles (7, 8) are used to lift the pharmaceutical carrier (4) on its support layer (3) free from the tray (2) and to prevent the support layer (3) from wrinkling. The exposed surface of the pharmaceutical carrier (4) is covered by a protector layer (9) which is also formed from a net-like material.

Figure 2:
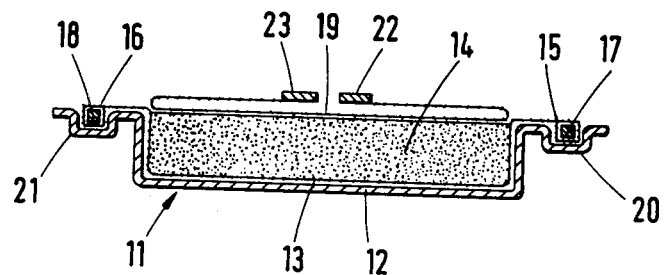
FIG. 2 is a cross-section through a second form of the dispenser of the present invention.

The dispenser (11) for a topically applied pharmaceutical composition which is shown in cross-section in FIG. 2 comprises a tray (12) which may be vacuum-moulded from a polypropylene-polyethylene copolymer. The tray (12) is lined with a support layer (13) which is in the form of a net-like material. A viscous pharmaceutical composition (14) is filled into the tray (12) to overlay the support layer (13) and to substantially fill the tray (12). The extra pieces of support layer (15, 16) which are capable of extending over the tops of two opposed edges are filled with a stiffening means (17, 18) in the form of a corrugated polystyrene strip.

The tray has been extended to include two smaller trays (20, 21) into which the stiffening means (17, 18) may rest prior to use. The exposed surface of the pharmaceutical carrier (14) is covered by a protector (19) which is folded back on itself and has two handling areas (22, 23) at its edge. The handling areas (22, 23) may be formed by adhering adhesive tape along the two edges of the protector (19). The presence of the handling areas (22, 23) facilitates removal of the protector (19) and reduces the risk of accidental contamination of the carrier during removal of the protector (19).

EXAMPLE 1

A tray, 18 cm×24 cm and 5 mm deep, was vacuum formed from a film of polypropylene-polyethylene copolymer. A piece of net material 18 cm×40 cm was placed in the bottom of the tray so that the net covered the base of the tray and the two sides and extended for 3 cm on two opposed edges. A piece of card 1 cm×18 cm was sealed into each of the extended areas to form stiff handles. The tray was then filled with an oil-in-water emulsion having the following formula,

| White petrolatum | 16.5% (w/w) |
| Stearyl alcohol | 15.3% |
| Isopropyl myristate | 6.6% |
| Sorbitan monostearate | 1.0% |
| Polyoxyl 40 stearate | 9.0% |
| Propylene glycol | 8.0% |
| Silver sulphadiazine | 1.0% |
| Deionised water | 42.6% | and prepared by the method described in Example 1 of U.S. Pat. No. 3,761,590. A protector layer of a net-like material 18 cm×24 cm was placed on top of the pharmaceutical carrier.

The tray, support layer and protector were presterilised using 2.5 Mrad gamma-irradiation. The oil-in-water emulsion was formed in a sterile manner. The oil-in-water emulsion was filled into the tray under aseptic conditions and packaged in a bacteria-proof and water-proof pouch.

In use the sterile tray and contents were removed from the pouch and the protector layer was peeled away from the pharmaceutical carrier. The support layer and the pharmaceutical carrier were lifted from the tray and the pharmaceutical carrier was carefully placed on the skin of a patient with a skin lesion. The support layer was carefully peeled away from the pharmaceutical carrier and the carrier covered by a gauze dressing in the normal way.

EXAMPLE 2

A cream was prepared in a similar manner to that described in Example 1 except that the antibacterial agent present was 2% of chlorhexidine digluconate. The cream was packaged in a dispenser of the invention.

EXAMPLE 3

A cream was prepared from the following ingredients

| Polyvinylpyrrolidone-iodine | 10% |
| Polethylene glycol (molecular weight 400) | 70% |
| Polyethylene glycol | 20% |

-continued (molecular weight 4000)

The cream was placed on a net support layer in a vacuum formed tray in a similar manner to that described in Example 1.

The tray, support layer, cream and protector were packaged in a bacteria-proof and water-proof pouch and sterilised by 2.5 Mrad gamma irradiation.

EXAMPLES 4 AND 5

Two non-medicated pharmaceutical carriers which are useful as emollient or moisturising creams were prepared from.

|  | Example 4 | Example 5 |
|---|---|---|
| Liquid paraffin | 25.0 (% w/w) | 35.0 (% w/w) |
| Petroleum jelly | 10.0 | — |
| Lanolin | 10.0 | 10.0 |
| White Beeswax | 12.0 | 17.0 |
| *Arlacel 60 | — | 2.0 |
| *Tween 60 | — | 3.0 |
| Borax | 0.7 |  |
| Water | 42.3 | 33.0 |

*Trade marks

The oil phase and the aqueous phase were each heated seperately to 75° C. (approx). The water phase was added to the oil phase and the mixture stirred until it had cooled to 50° C. and was then poured onto a net support layer in a vacuum formed tray. On cooling to ambient room temperature the creams could be lifted from the tray on the support layer.

EXAMPLE 6

A zinc oxide/castor oil cream was prepared from the following ingredients.

| White Beeswax | 10.0 (% w/w) |
|---|---|
| Cetastearyl alcohol | 2.0 |
| Castor oil | 50.0 |
| Zinc oxide | 7.5 |
| Arachis oil | 30.5 |

All the components except zinc oxide are mixed together and the temperature raised to 75° C. The mixture is allowed to cool to 50° C. and the zinc oxide is added and stirring continued to form an homogenious ointment. The cream was then placed on a net support layer on a polyethylene tray. At ambient temperature the cream may be lifted from the tray on the support layer.

What is claimed:

1. A dispenser for a viscous pharmaceutical composition which dispenser comprises a tray, a support layer which covers the base and at least two opposed sides of the tray and is capable of extending over the top edges of said sides of the tray, a viscous pharmaceutically acceptable carrier which overlies the support layer and which may be lifted from the tray on the support layer and a removable protector layer covering the exposed surface of the pharmaceutically acceptable carrier, and in which the pharmaceutically acceptable carrier adheres more strongly to the support layer than to the protector layer.

2. A dispenser according to claim 1 in which the viscous pharmaceutically acceptable carrier contains a medicament.

3. A dispenser according to claim 2 in which the pharmaceutically acceptable carrier contains from 1 to 12.5% by weight of antibacterial agent.

4. A dispenser according to claim 3 in which the antibacterial agent is silver sulphadiazine.

5. A dispenser according to claim 1 in which the viscous pharmaceutically acceptable carrier is an oil-in-water emulsion.

6. A dispenser according to claim 1 in which the viscous pharmaceutically acceptable carrier is a self-supporting gel.

7. A dispenser according to claim 1 in which the viscous pharmaceutically acceptable carrier is a hydrophobic ointment.

8. A dispenser according to claim 1 in which the tray is formed from a vacuum mouldable polymeric material.

9. A dispenser according to claim 1 in which the tray has a depth of from 2.5 to 8.0 mm.

10. A dispenser according to claim 1 in which the carrier comprises a net-like material which has been formed by stretching of an embossed film to cause fibrillation.

11. A dispenser according to claim 1 in which the two opposed extended parts of the support layer each carries a stiffened portion as a handle to facilitate lifting of the support layer and pharmaceutically acceptable carrier from the tray.

12. A dispenser according to claim 1 in which the protector layer comprises a net-like material.

13. A dispenser according to claim 1 which is sterile and which is packaged in a bacteria-proof and water-proof package.

14. A method of treatment of an animal which comprises applying to the skin of the animal a viscous pharmaceutically acceptable carrier when dispensed from a dispenser which comprises a tray, a support layer which covers the base and at least two opposed sides of the tray and is capable of extending over the top edges of said sides of the tray, the said carrier which overlies the support layer and a removable protector layer which covers the exposed surface of the said carrier and in which the said carrier adheres more strongly to the support layer than to the protector layer, which method comprises peeling the protector layer from the surface of the said carrier, lifting the support layer and the said carrier from the tray, inverting to apply said carrier to the skin and peeling off the support layer.

15. A method according to claim 14 in which the support layer and the said carrier are lifted by means of handles present at two opposed edges of the support layer.

16. A method according to claim 15 in which the said carrier contains from 1 to 12.5% of antibacterial agent.

17. A method according to claim 16 in which the antibacterial agent is silver sulphadiazine.

* * * * *